Feb. 1, 1949. T. J. ANDRE Plant Pat. 822
ROSE PLANT
Filed Feb. 14, 1947
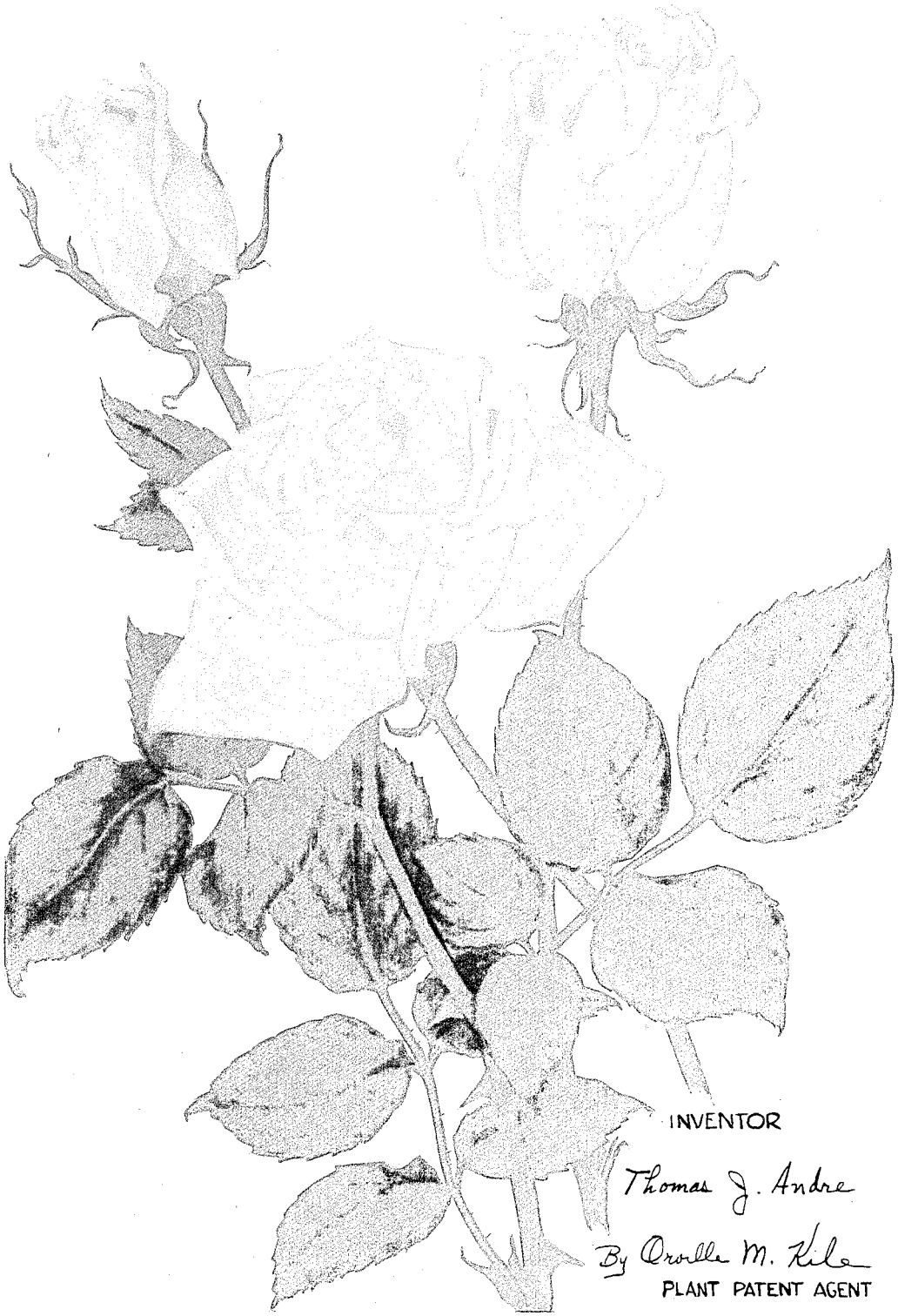
INVENTOR
Thomas J. Andre
By Orville M. Kile
PLANT PATENT AGENT Patented Feb. 1, 1949

Plant Pat. 822

UNITED STATES PATENT OFFICE

822

ROSE PLANT

Thomas J. Andre, Doylestown, Pa., assignor to Andre Greenhouses, Inc., Doylestown, Pa., a corporation of Pennsylvania Application February 14, 1947, Serial No. 728,465

1 Claim. (Cl. 47—61)

My present discovery pertains to a new and distinct variety of hybrid tea rose plant of the general "Talisman type," and originated as a sport of Yellow Gloria (Plant Patent No. 240), discovered in a greenhouse by me at Doylestown, Pennsylvania.

While the color combination differs from that of any rose variety known to me, this is particularly evident in the bud which contains considerably more orange than other known Talisman type roses including Yellow Gloria, and this deep orange shade is almost uniform over the outer surface of the bud. The bud is distinctive also in that it is much larger with larger petals and tapering point.

The open rose contains a great deal of the pink tones, particularly on the petal edges. Although essentially pink in the full-blown stage, much orange is evident, particularly toward the center of the petals.

Another outstanding feature of this new variety is the difference in growth habits with regard to temperature. Other Talisman type roses known to me, including the Yellow Gloria, are run cooler than most other hybrid tea roses in order to give them a strong stem and larger bud. But my new rose can and must be run warm to produce the excellent growth and a good large bud.

The best cutting stage for my new rose is with the calyx dropped, while with most Talisman type roses the best time to cut is when the calyx is still in place on the bud.

All these features, together with strong stems and a continuous blooming season, combine to make a very desirable variety both for cut flowers and for garden use.

The original sport has been asexually reproduced and its novel characteristics have proved to be permanent.

The accompanying illustration shows in approximately their true colors, three typical specimens in various stages of opening, together with a portion of the stems and foliage.

Following is a detailed description of the plant and flower, color plate references indicating Ridgway's Color Standards and Nomenclature.

*The plant*

Growth habits: Very strong and free grower. Breaks back easily from either a hard cut or a cut from the first terminal leaf above the node. Grows best when run warm.

Blooming habits: Continuous bloomer, but has a tendency to produce better in summer than in the cooler weather.

Foliage: Very distinctive type of foliage for the "Talisman" type rose. It is much heavier, darker and larger than that of the family from which it originated, but not so heavy or so large or of so dark a color as foliage of the Briarcliff type.

*Leaflets.*—3 to 5.

*Shape.*—Oval with acuminate apex and obtuse base. Edge sharply serrate.

*Color.*—Dark clear green. Forest Green (Plate XVII) or darker on upper surface, with under surface approximately Bice Green (Plate XVII).

*Size.*—Medium.

*Aspect.*—Dull to semi-glossy.

*Texture.*—Medium to heavy.

*Rachis.*—Slender; short; grooved above.

*Stipules.*—Short; narrow; clinging.

Stems: Very strong; lighter than foliage in color.

*The flower*

Bud:

*Size.*—Large for the Talisman type rose, having more and large petals.

*Form.*—Long and tapering, opening somewhat urn-shaped.

*Color.*—In the tight bud the color is almost a uniform deep orange color, which is a distinctive feature in a varicolored rose. While still retaining its tapered conical shape, the predominating color lies between Peach Red (Plate I) and Grenadine (Plate II). Later as the bud opens, the color lightens.

*Peduncle.*—Short; slender; light green, covered with small spines.

Blossom:

*Borne.*—Singly.

*Form.*—High centered. Petals well placed. Later opens into cupshape. Petals recurve slightly at edge but do not roll.

*Size.*—Medium to large. Averages about 4½ to 5 inches in diameter.

*Petalage.*—Double, numbering 24 to 30 petals.

*Arrangement.*—Regular.

*General color effect.*—In the full-blown stage the rose is predominantly pink, ranging from Thulite Pink (Plate XXVI) at the edges of the outer petals, to Eosine Pink (Plate I) deep in the center. Orange tones spread from the edge of the petals to the deep yellow aiglet.

Petals:

*Texture.*—Soft and velvety to touch. Medium in weight.

*Shape.*—Almost round; deeply cupped.

*Size.*—Outer petals are approximately 1¾ inches across in each direction in a typical specimen.

*Color.*—Pink tones at edge, light orange tones in center, and deep yellow aiglet on inner surface.

Longevity: Flower lasts from 6 to 10 days, depending upon conditions under which it is kept.

Permanence: Color remains without fading for many days. Petals cling tenaciously until dead.

Fragrance: Mildly fragant.

Having thus disclosed my discovery, I claim:

The new and distinct variety of hybrid tea rose plant of the general Talisman type, substantially as herein shown and described, characterized particularly by its strong and free growth habits and continuous blooming habits; its need for warmer temperatures to secure best blooming results; its larger, heavier and darker foliage for Talisman type rose; its strong stems; its large, long, tapering bud almost uniformly deep orange in color; and its flowers of pink and orange tones which last unusually well without fading.

THOMAS J. ANDRE.

No references cited.